| United States Patent [19] | [11] | 4,332,894 |
|---|---|---|
| Whistler | [45] | Jun. 1, 1982 |

[54] CONVERSION OF GUAR GUM TO GEL-FORMING POLYSACCHARIDES BY THE ACTION OF α-GALACTOSIDASE

[75] Inventor: Roy L. Whistler, West Lafayette, Ind.

[73] Assignee: Purdue Research Foundation, West Lafayette, Ind.

[21] Appl. No.: 178,507

[22] Filed: Aug. 15, 1980

[51] Int. Cl.$^3$ .................. C12P 19/04; C12P 19/14
[52] U.S. Cl. ........................... 435/99; 435/101;
435/274; 426/48; 426/52; 426/573
[58] Field of Search .............. 435/99, 101, 208, 274;
426/48, 52, 573

[56] References Cited

U.S. PATENT DOCUMENTS 3,297,604  1/1967  Germino .................. 435/101 X

*Primary Examiner*—Esther M. Kepplinger
*Attorney, Agent, or Firm*—John R. Nesbitt; Robert E. Harris

[57] ABSTRACT

Water-soluble polysaccharide guar gum, guaran, is altered to convert its properties from those of producing a highly viscous stable dispersion to enable production of a sequence of products that may be separately produced through the selective removal of D-galactopyranosyl side units so as to produce different lengths of molecular segments containing no derivatizing α-D-galactopyranosyl groups. The structure therefore yields a high viscosity polysaccharide with the ability to form gels of various strengths ranging from very weak gels to strong gels by appropriate selection of the extent to which the α-D-galactopyranosyl groups are removed.

2 Claims, 5 Drawing Figures

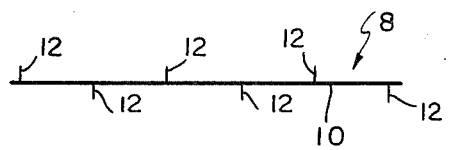
FIG. 1
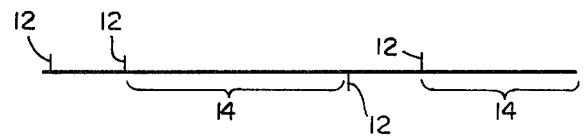
FIG. 2
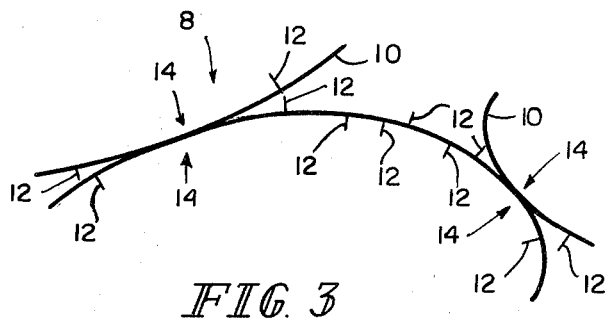
FIG. 3
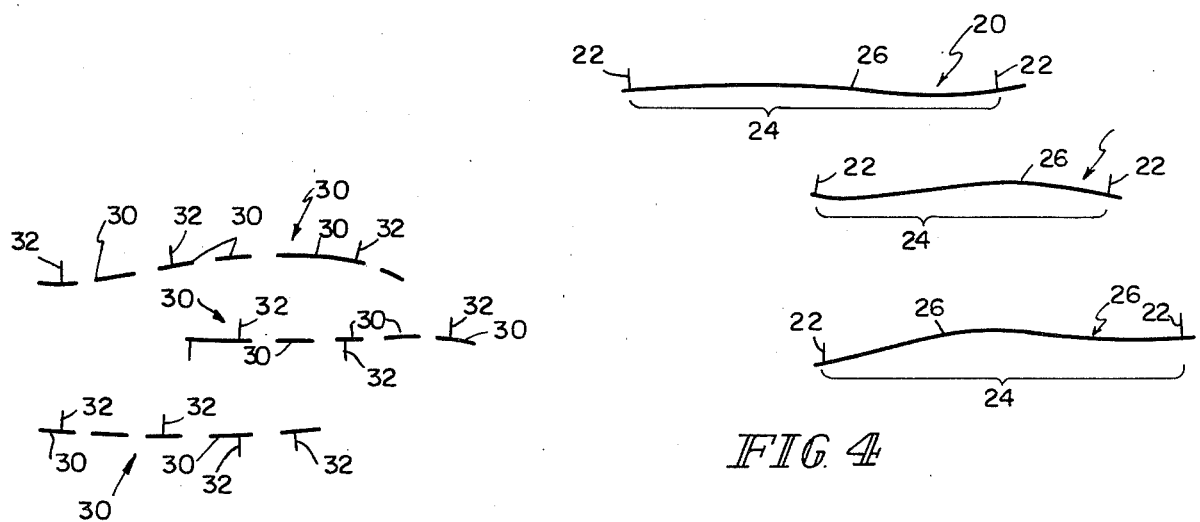
FIG. 4
FIG. 5

CONVERSION OF GUAR GUM TO GEL-FORMING POLYSACCHARIDES BY THE ACTION OF α-GALACTOSIDASE

This invention relates to gel-forming polysaccharides, and particularly to a mechanism by which guar gum can be converted to gel-forming polysaccharides similar to locust bean gum polysaccharide.

Guar gum is 78–82% of the endosperm component of guar seed (see "Guar: Agronomy, Production, Industrial Use and Nutrition" by Roy L. Whistler and Theodore Hymowitz, Purdue University Press, West Lafayette, IN, 1979). Guar is *Cyanopsis tetragonolobus*, of the family Leguminosae. Guar has been grown for centuries in India and Pakistan, where it is one of the crops used as a food for both humans and animals. In the United States, it is grown in north Texas and southern Oklahoma, Guar seeds contain approximately 14–17% hull, 35–42% endosperm, and 43–47% germ. They are commonly dry-milled to separate out the endosperm which is the industrial guar gum of commerce (see "Industrial Gums", Roy L. Whistler, editor, Academic Press, New York, 1973). Although guar gum is normally commercially used in its commercially produced crude form as the ground endosperm containing small amounts of cellulose, protein, and other impurities, its principal component and the component giving it industrial value is the polysaccharide guaran. Guaran is a galactomannan consisting of 34.6% D-galactopyranosyl units and 63.4% D-manopyranosyl units. Guaran has been shown to have a structure of 1→4-linked β-D-manopyranosyl units, with every second chain sugar unit bearing a single α-D-galactopyranosyl unit linked 1→6. As a consequence, guaran readily dissolves in water to form highly viscous solutions even at low concentrations of gum. The solutions remain stable because molecular segments of guaran cannot bind to each other when they collide in solution. This occurs essentially since the manopyranosyl chains are separated from each other by the derivatizing α-D-galactopyranosyl side groups.

Another important industrial gum is locust bean gum. This gum is derived from locust bean or carob seeds. These are the seeds from the *Ceratonia siliqua* plant. The plant belongs to the family Leguminosae, subfamily Caesalpiniaceae. The ground endosperm of the carob tree seed or the locust bean is also a galactomannan widely used in industry. "Industrial Gums", supra. Locust bean and carob seed gum have many of the properties of guar gum but, in addition, have a tendency to gel and synergistically to produce gels in combination with certain other gums such as xanthan gum and carrageenan. An examination of the structure of carob seed gum or locust bean gum (C. W. Baker and R. L. Whistler, "Distribution of D-galactopyranosyl Groups in Guaran and Locust Bean Gum", 45 *Carbohydrate Research*, 237–243 [1975]) demonstrates that the structure of carob seed gum or locust bean gum differs from that of guaran in that the D-galactopyranosyl groups are not evenly distributed along the chains as they are in guaran, but rather are irregularly grouped along the chain, so that on the average, 25 D-galactopyranosyl groups are grouped together with an intermediate stretch of some 85 adjacent denuded D-manopyranosyl units in between. It thus appears that the long chains of 85 or so adjacent denuded D-manopyranosyl units associate intermolecularly in solution to form junction zones which promote formation of weak gel structures. It further appears that the same denuded segments of chain may also combine with segments of xanthan gum and carrageenan gum to produce cross-linked gel structures. It further appears that by variations in the length of the denuded chain segment exposed, variations in the strength of the gel could be predicted and achieved. Essentially, a gel having a desired strength for a particular application, ranging from a weak gel to a strong gel, could be prepared by shortening, or lengthening, respectively, the denuded molecular segments (that is, the segments containing no D-galactopyranosyl groups).

According to the invention, guar gum can be modified through the use of enzymes, for example, a commercially available α-D-galactosidase enzyme. This α-D-galactosidase enzyme is useful to remove the α-D-galactopyranosyl side groups. In modification of guar gum, by controlling the length of time that the guar gum is exposed to the α-D-galactosidase enzyme, and therefore by controlling the extent of the removal of the α-D-galactopyranosyl side groups, the length of denuded mannan chain exposed by the enzyme's activity on the guar gum can be controlled. Of course, control of the length of denuded mannan chain exposed provides a direct control on the amount of intermolecular association that adjacent guaran molecules in solution experience. To control this amount of intermolecular association is, of course, to control the relative strength or weakness of a gel produced from guar gum by the activity of the α-D-galactosidase enzyme.

Commercial D-galactosidase enzymes are available from various sources. Of course, it is important that the D-galactosidase enzymes used do not contain mannosidases which would cleave the principal mannan backbone or chain of the guaran. Breaking of the mannan backbone or chain lowers the viscosity of the solution to levels unacceptable for certain important industrial applications. If commercial D-galactosidase enzymes containing no mannosidase enzymes are unavailable, mannosidase enzyme-free D-galactosidase enzymes can be produced from germinated guar seeds. The resulting galactosidase enzyme can be separated from any mannosidase enzymes present by fractional precipitation from solution by varying the concentration of ammonium sulfate, or by gel filtration techniques known in enzyme chemistry.

As previously mentioned, the limitation in the use of galactosidase enzyme on guaran is the amount of time that the guaran is exposed to the activity of the galactosidase enzyme. If the period of exposure is too long, all of the α-D-galactopyranosyl side chains will be stripped away, leaving only a mannan backbone chain which will join with other mannan chains to form an insoluble precipitate. Such an extended degree of hydrolysis produces an essentially useless product. Therefore, according to the invention, low concentrations of galactosidase enzyme are used, and they are used only for carefully controlled periods of time. Higher concentrations of galactosidase enzyme can be used to treat the guaran, but the higher concentrations require somewhat more carefully controlled reaction times. Reaction time will vary depending upon whether the galactosidase enzyme is added to an aqueous solution of guar gum or guaran, or whether the enzyme is fixed, or immobilized, by any one of a number of methods for immobilizing enzymes known in the enzyme industry. If the enzyme is immobilized on a support, the amount of guar gum or guaran that is passed over the enzyme support to be exposed to enzyme activity can be controlled by the volume of flow. The contact period between the guar gum or guaran and the enzyme can thereby be carefully controlled.

The precise conditions of use for a particular galactosidase enzyme depend upon the concentration of the galactosidase enzyme and upon the activity of the enzyme. Both of these factors depend, in turn, upon whether the enzyme is added to the aqueous solution of guar gum or guaran, or whether the enzyme is fixed, and, if fixed, the methods of fixation and configuration of the bed. Consequently, it is believed best to treat the guar gum or guaran with galactosidase enzyme in a batch process, by which the enzyme is added directly to a test solution of guaran or guar gum. Alternatively, a test solution of guaran or guar gum can be exposed to the immobilized enzyme fixed bed. Test runs can be made for different time intervals and the degrees of gel formation at the end of each test run can be determined. A graph can be generated for a particular concentration of guaran or guar gum in solution showing degree of gel formation versus time. When several solutions of guar gum or guaran have been treated with the enzyme and the tests giving the desired results have been identified, further preparations utilizing the thus-determined treatment parameters can be made to yield guar gum or guaran gels of the desired strength.

In an illustrative preparation technique, guar gum is treated with a commercially available D-galactosidase enzyme, and a 1% by weight solution of the treated guaran or guar gum in water is permitted to stand for thirty minutes. At the end of thirty minutes, a viscosity measurement is conducted. A reduction, and specifically a large reduction, in the viscosity of the solution indicates the presence of mannosidase enzymes in the starting enzyme treatment. The mannosidase enzymes have cleaved, or broken, the mannan backbone or main chain of the guaran and rendered the treated solution useless. On the other hand, gel formation in the 1% solution after standing for thirty minutes will be indicated by an increase in the viscosity of the 1% solution. The promotion of gel-forming characteristics in the 1% solution, and the relative "strength" of the resultant gel, can be made by any of a number of methods for measuring gel strength known in the industry.

Another method for measuring the success of the treatment with D-galactosidase enzyme is the change in viscosity of the treated guaran or guar gum when a standard concentration of the treated guaran or guar gum is mixed with a standard concentration of a synergistically active gum such as xanthan gum of carrageenan. The synergistic increase in viscosity of a mixture of these two normally water-soluble polysaccharides will be indicative of the degree of removal of D-galactopyranosyl side groups by D-galactosidase enzyme.

The invention may further be understood by reference to the drawings and the accompanying descriptions of the drawings.

FIG. 1 illustrates diagrammatically guaran molecules 8, each consisting of a mannan main chain 10 with spaced galactopyranosyl side groups 12.

FIG. 2 illustrates the guaran molecules 8 after treatment with galactosidase enzyme. Each includes a mannan main chain 10, fewer galactopyranosyl side units 12 and vacant, or denuded, sections 14 for junction zone formation.

FIG. 3 illustrates the treated guaran molecules 8 of FIG. 2 associated intermolecularly to produce a gel. Again, each treated guaran molecule includes the mannan main chain 10, galactopyranosyl side units 12, and junction zones 14. The junction zones 14 of the treated guaran molecules lie in contact, or closely adjacent, one another in a manner forming the gel.

FIG. 4 illustrates guaran molecules 20 treated excessively with galactosidase enzyme. The inordinately long junction zones 24 in these molecules 20 are to be noted. As previously mentioned, in this excessively treated guaran, essentially only the mannan main chain 26 remains. The essentially completely denuded mannan main chains 26 with very few, or no, remaining galactopyranosyl side units 22 associate intermolecularly to form insoluble precipitates which have little value.

FIG. 5 illustrates the result of treatment of guaran including mannan backbones or main chains 30 with enzyme mixtures including both a D-galactosidase enzyme and a mannosidase enzyme. It is to be noted that, although not all of the galactopyranosyl units 32 have been removed, the mannan backbone chains 30 have been attacked by the mannosidase in the treating enzyme mixture, cleaving them and resulting in a low viscosity solution of little utility. This drawing illustrates the importance of isolation of the galactosidase enzymes, or at the very least, separation of the undesirable mannosidase enzymes from the treating enzyme mixture.

What is claimed is:

1. A method of treatment of guaran having a chain or backbone to which side groups are attached, the treatment to render the guaran chain more susceptible to association intermolecularly with other guaran chains, thereby promoting gel formation in the treated guaran, the treatment including the steps of:

isolating an enzyme or mixture of enzymes which act to break the bonds between the side groups and the guaran chain;

treating the guaran with the enzyme or enzymes to break such bonds and remove the side groups from the guaran chain to denude zones of desired length along the guaran chain; and removing the enzyme or enzymes from active contact with the guaran when zones of desired length have been established to prevent further enzyme activity on the partially denuded guaran.

2. A method of treating guaran to cause it to form a gel having a desired strength, comprising treating the guaran with a α-D-galactosidase enzyme for a period of time sufficient to remove α-D-galactopyranosyl side chains to denude zones of desired length of the mannan main chain or backbone of the guaran, removing the α-D-galactosidase enzyme from active contact with the treated guaran to prevent total denuding of the mannan chain of galactose groups, and bringing the treated guaran into contact with other treated guaran molecules to permit intermolecular association in the denuded zones and cause gel formation.

* * * * *